US00PP13893P29

(12) United States Plant Patent
Oudolf

(10) Patent No.: US PP13,893 P2
(45) Date of Patent: Jun. 17, 2003

(54) ECHINACEA PLANT NAMED 'VINTAGE WINE'

(75) Inventor: Petrus Hendricus Oudolf, Hummelo (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,967

(22) Filed: May 6, 2002

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,242 P2 * 12/2001 Hawks ..... Plt./263

OTHER PUBLICATIONS

UPOV ROM GTITM Computer Database, GTI JOUVE retrieval software 2002/02, citation(s) for 'Vintage Wine'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Echinacea plant named 'Vintage Wine', characterized by its upright plant habit; freely flowering habit and red-purple-colored ray florets and dark red-tipped disc florets.

1 Drawing Sheet

BOTANICAL CLASSIFICATION/CULTIVAR DESIGNATION

*Echinacea purpurea* cultivar Vintage Wine.

BACKGROUND OF THE INVENTION

The present Invention relates to a new and distinct cultivar of Echinacea plant, botanically known as *Echinacea purpurea*, and hereinafter referred to by the name 'Vintage Wine'.

The new Echinacea was discovered as a chance seedling of two unidentified selections of *Echinacea purpurea*, not patented. The new Echinacea was discovered and selected by the Inventor in 1997 as a single flowering plant in a controlled environment in Hummelo, The Netherlands.

Asexual reproduction of the new Echinacea by divisions was first conducted in Hummelo, The Netherlands in 1997. Since then, asexual reproduction by divisions has shown that the unique features of this new Echinacea are stable and reproduced true to type in successive generations.

SUMMARY OF THE INVENTION

The cultivar Vintage Wine has not been observed under all possible environmental conditions. The phenotype may vary somewhat with variations in environment such as temperature and light intensity without, however, any variance in genotype.

The following traits have been repeatedly observed and are determined to be the unique characteristics of 'Vintage Wine'. These characteristics in combination distinguish 'Vintage Wine' as a new and distinct Echinacea:

1. Upright plant habit.
2. Freely flowering habit.
3. Red purple-colored ray florets and dark red-tipped disc florets.

Plants of the new Echinacea differ primarily from plants of the parent selections in ray and disc floret coloration.

Plants of the new Echinacea can be compared to plants of the Echinacea cultivar Magnus, not patented. However, plants of the new Echinacea have more upright ray florets than plants of the cultivar Magnus. In addition, plants of the new Echinacea and the cultivar Magnus differ in ray floret coloration.

BRIEF DESCRIPTION OF THE PHOTOGRAPH

The accompanying colored photograph illustrates the overall appearance of the new Echinacea showing the colors as true as it is reasonably possible to obtain in colored reproductions of this type. Colors in the photograph may differ from the color values cited in the detailed botanical description which accurately describe the colors of the new Echinacea. The photograph comprises a side perspective view of a typical flowering plant of 'Vintage Wine' grown in an outdoor nursery.

DETAILED BOTANICAL DESCRIPTION

The aforementioned photograph and following observations and measurements describe plants grown in Lisserbroek, The Netherlands, in an outdoor nursery under full sun conditions. In August, when plants were about two years old, the photograph and the observations and measurements were taken. Color references are made to The Royal Horticultural Society Colour Chart, 2001 edition, except where general terms of ordinary dictionary significance are used.

Botanical classification: *Echinacea purpurea* cultivar Vintage Wine.

Parentage:

*Female, or seed, parent.*—Unidentified selection of *Echinacea purpurea*, not patented.

*Male parent, parent.*—Unidentified selection of *Echinacea purpurea*, not patented.

Propagation:

*Type.*—By divisions.

*Time to produce a rooted plant.*—About two months.

*Root description.*—Fine fibrous and well-branched.

Plant description:

*Appearance.*—Perennial herbaceous container and garden plant. Upright plant habit; narrow inverted triangle. Basal branches with about three lateral branches each; dense and full plants. Moderately vigorous growth habit.

*Plant height.*—About 80 cm.

*Plant width or area of spread.*—About 65 cm.

*Lateral branches.*—Length: About 28 cm. Diameter: About 4 mm. Internode length: About 2 cm. Aspect: Mostly upright. Strength: Strong. Texture: Sparsely pubescent; rough. Color: 146A to 146B.

*Foliage description.*—Arrangement: Alternate; single. Length: About 19 cm. Width: About 8 cm. Shape: Elliptic to narrowly ovate. Apex: Acute. Base: Cuneate. Margin: Irregularly serrate. Venation pattern: Pinnate. Texture, upper and lower surfaces: Pubescent; rough. Color: Young foliage, upper surface: 137A to 137B. Young foliage, lower surface: 137B to 137C. Fully expanded foliage, upper surface: 139A. Fully expanded foliage, lower surface: 137A to 137B. Venation, upper surface: 144B. Venation, lower surface: 144C to 144D. Petiole: Length: About 2.1 cm. Diameter: About 2 mm. Texture, upper and lower surfaces: Smooth. Color, upper and lower surfaces: 144A.

Inflorescence description:

*Appearance.*—Terminal and axillary inflorescences held mostly above and beyond the foliage on strong peduncles. Composite inflorescence form, radially symmetrical; oblanceolate-shaped ray florets; disc florets massed at the center; ray and disc florets arranged acropetally on a capitulum. Inflorescences persistent. Inflorescences face mostly upright.

*Flowering response.*—Plants flower continuous and freely from late July to late September in Lisserbroek, The Netherlands.

*Postproduction longevity.*—Inflorescences maintain good color and substance for about five days on the plant when grown in an outdoor environment. As a cut flower, inflorescences maintain good color and substance for about two weeks in an interior environment.

*Quantity of inflorescences.*—Freely flowering; about ten open inflorescences per plant at one time.

*Fragrance.*—Faint, sweet.

*Inflorescence bud (at stage of showing color).*—Length: About 3.5 cm. Diameter: About 3.3 cm. Shape: Narrowly ovoid. Color: 175A.

*Inflorescence size.*—Diameter: About 8 cm. Depth (height): About 3.5 cm. Disc diameter: About 3.5 cm.

*Ray florets.*—Length: About 3 cm. Width: About 8 mm. Shape: Oblanceolate. Apex: Emarginate to acute. Base: Acute. Margin: Entire. Texture: Smooth. Orientation: Initially upright then about 60° from vertical. Number of ray florets per inflorescence: About 40 in one to two whorls. Color: When opening, upper surface: 61C to 63A. When opening, lower surface: 63A. Fully opened, upper surface: 61C to 61A. Fully opened, lower surface: 60A.

*Disc florets.*—Shape: Tubular, elongated. Apex: Five-pointed; acute. Length: About 1.1 cm. Width: About 1 mm. Number of disc florets per inflorescence: More than 200. Color, immature and mature: 143B; towards the base, close to 155D; towards the apex, N25C; apex, 46A.

*Phyllaries.*—Length: About 7 mm. Diameter: About 3 mm. Shape: Lanceolate. Apex: Narrowly acute. Base: Fused. Margin: Entire. Texture: Densely pubescent. Number per inflorescence: About 40 in about six whorls. Color, upper surface: 137A. Color, lower surface: 143A.

*Peduncles.*—Length: About 18 cm. Diameter: About 4 mm. Angle: Mostly erect. Strength: Strong. Texture: Sparsely pubescent; rough. Color: 144A.

*Reproductive organs.*—Androecium: Present on disc florets only. Stamen number: Five per floret; basifixed. Anther shape: Narrowly oblong. Anther length: About 1 mm. Anther color: Close to N199A. Pollen amount: Moderate. Pollen color: 17B to 17C. Gynoecium: Present on both ray and disc florets. Pistil number: One per floret. Pistil length: About 7 mm. Stigma shape: Two-parted. Stigma color: 187A. Style length: About 6 mm. Style color: N144B. Ovary color: 150D to 157A.

*Fruit.*—Type: Flattened achene. Quantity per inflorescence: One. Length: About 5 mm. Diameter: About 1 mm. Color: N199A to N200A.

*Seed.*—Yield: High, almost all inflorescences produce viable seed. Quantity of seed per fruit: One. Length: About 5 mm. Diameter: About 1 mm. Color: N199A to N200A.

Disease/pest resistance: Resistance to pathogens and pests common to Echinaceas has not been observed on plants grown under outdoor conditions.

Temperature tolerance: Plants of the new Echinacea have been observed to tolerate temperatures from about −12 to 35° C.

It is claimed:

1. A new and distinct cultivar of Echinacea plant named 'Vintage Wine', as illustrated and described.

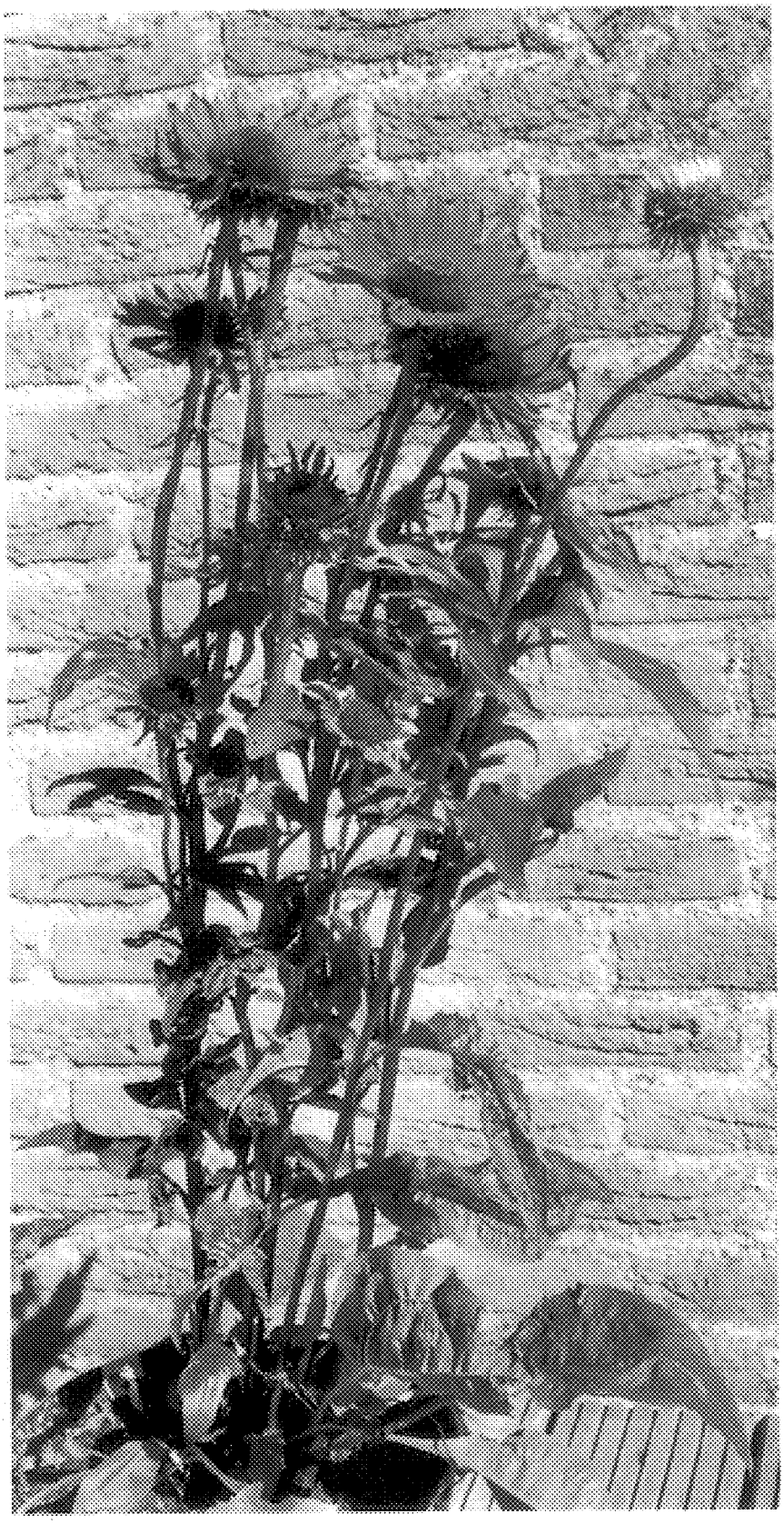

* * * * *